(12) United States Patent
Nawata et al.

(10) Patent No.: US 6,803,206 B2
(45) Date of Patent: Oct. 12, 2004

(54) METHOD FOR IDENTIFYING ENDOCRINE DISRUPTORS AND KIT FOR CARRYING OUT THE SAME

(75) Inventors: Hajime Nawata, Higashi-ku (JP); Toshihiko Yanase, Higashi-ku (JP)

(73) Assignee: Otsuka Pharmaceutical Co., Ltd., Osaka (JP)

(*) Notice: Subject to any disclaimer, the term of this patent is extended or adjusted under 35 U.S.C. 154(b) by 222 days.

(21) Appl. No.: 10/029,862

(22) Filed: Dec. 31, 2001

(65) Prior Publication Data

US 2003/0124641 A1 Jul. 3, 2003

(51) Int. Cl.$^7$ .............................. C12Q 1/26; C12Q 1/02
(52) U.S. Cl. .......................................... 435/25; 435/29
(58) Field of Search ..................................... 435/25, 29

(56) References Cited

PUBLICATIONS

Kitawaki et al., "Growth Suppression of MCF–7 Human Breast Cancer Cells by Aromatase Inhibitors: A New System for Aromatase Inhibitor Screening" (1993) J. Steroid Biochem. Molec. Biol., 44(4–6), 667–670.*
Powlin et al., "Ex Vivo and In Vitro Testis and Ovary Explants: Utility for Identifying Steroid Biosynthesis Inhibitors and Comparison to a Tier I Screening Battery" (1998) Toxicological Sciences, vol. 46, 61–74, Abstract.*
Stresser et al., "A High–Throughput Screen to Identify Inhibitors of Aromatase (CYP19)" (Sep. 10, 2000) Anal. Biochem. 284(2), 427–430.*
Okubo et al., "Down–Regulation of Promoter 1.3 Activity of the Human Aromatase Gene in Breast Tissue by Zinc–finger Protein, Snail (SnaH)" (Feb. 15, 2001) Cancer Research, 61, 1338–1346.*
Yang et al., "Two Organochlorine Pesticides, Toxaphene and Chlordane, Are Antagonists for Estrogen–related Receptor–1 Orphan Receptor" (Sep. 15, 1999) Cancer Research, 59, 4519–4524.*
Almstrup et al. "Dual Effects of Phytoestrogens Result in U–Shaped Dose–Response Curves" (Jun. 2002) Environ. Health Perspect., vol. 110, pp. 743–748*

Zacharewski, T. "Identification and Assessment of Endocrine Disruptors: Limitations of in Vivo and in Vitro Assays" (Apr. 1998) Environ. Health Perspect. 106(Suppl 2), 577–582.*
Mak et al., "A Yeast Screen System for Aromatase Inhibitors and Ligands for Androgen Receptor: Yeast Cells Transformed with Aromatase and Androgen Receptor" (1999) Environ. Health Perspect., 107, 855–860.*
Chen et al., "Breast Tumor Aromatase: Functional Role and Transcriptional Regulation" (1999) Endocrine–Related Cancer, 6, 149–156.*
Saitoh et al, *Biochem. Biophys. Res. Comm.*, 289:198–204 (2001).
Nishi et al, *Endocrinology*, 142(1):437–445 (2001).
KGN Cell Line (http://www.ric.riken.go.jp/cgi–bin/CELL/cell.p1? DATA=314).
RGN Animal Cell Line Catalog, General Catalog No. 5–1, p. 158 (May 2001).
Mu et al, *Mol. Cell. Endrocrin.*, 181:239–248 (2001).
Mu et al, *Endocrinology*, 142(8):3590–3597 (2001).
Mu et al, *Biochem. Biophys. Res. Comm.*, 271:710–713 (2000).
Nawata et al, *J. Steroid Biochem. Molec. Biol.*, 53(1–6):165–174 (1995).
Rainey et al, *J. of Clin. Endocrin. Metabol.*, 78(3):705–710 (1994).
Nawata et al, 76$^{th}$ *Annual Meeting Program and Abstracts of the Annual Meeting–Endocrine Society*, "Aromatase Activity in Human Osteoblast–Like Osteosarcoma Cell", No. 1195 (1994) title only.
Tanaka et al, *Calcif Tissue Int.*, 52:107–109 (1993).
Steinkampf et al, *Mol. Endocrinology*, 1(7):465–471 (1987).
Simms et al, *Cancer Res.*, 40:4356–4363 (1980).
Nawata, "Effects of Endocrine Disruptors on Aromatase Activity in the Human Ovary Granulosa–like Cell Line KGN", Endocrine Disruptors The First Symposium on Each Category, Lecture Summary (Sep. 19, 2002), partial english transl.

* cited by examiner

*Primary Examiner*—Jon P. Weber
(74) *Attorney, Agent, or Firm*—Sughrue Mion, PLLC

(57) ABSTRACT

A method for identifying an endocrine disruptor using a cell line having aromatase activity, particularly, a human granulosa-like tumor cell line; and a kit for carrying out the method is disclosed.

5 Claims, 5 Drawing Sheets

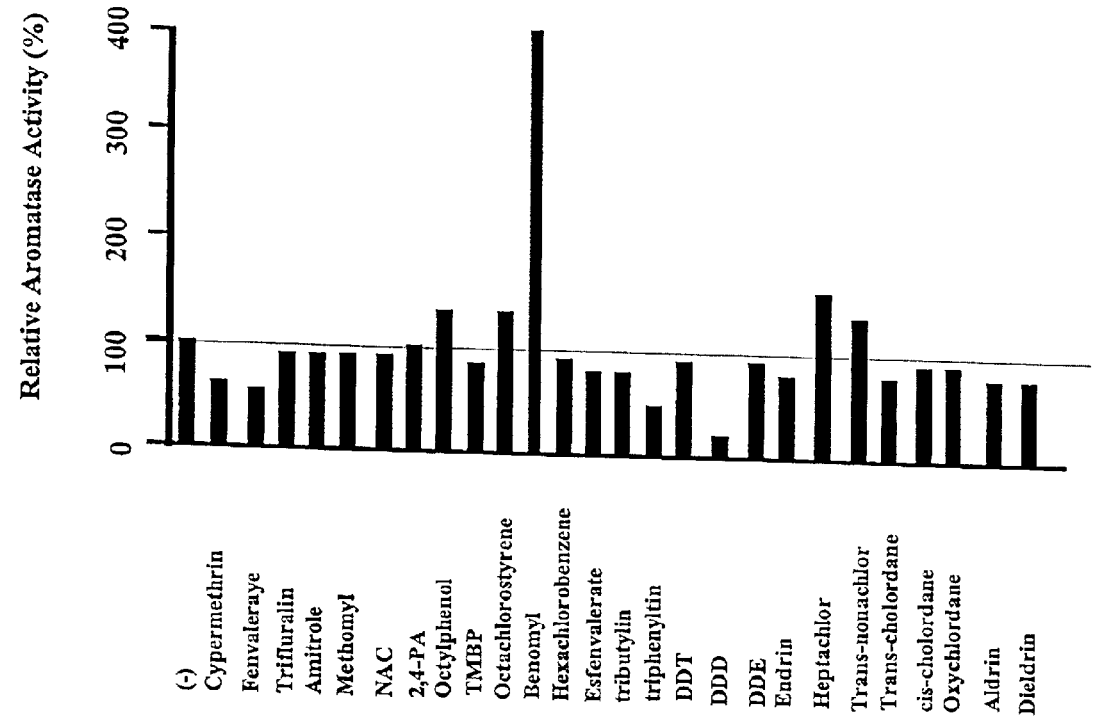
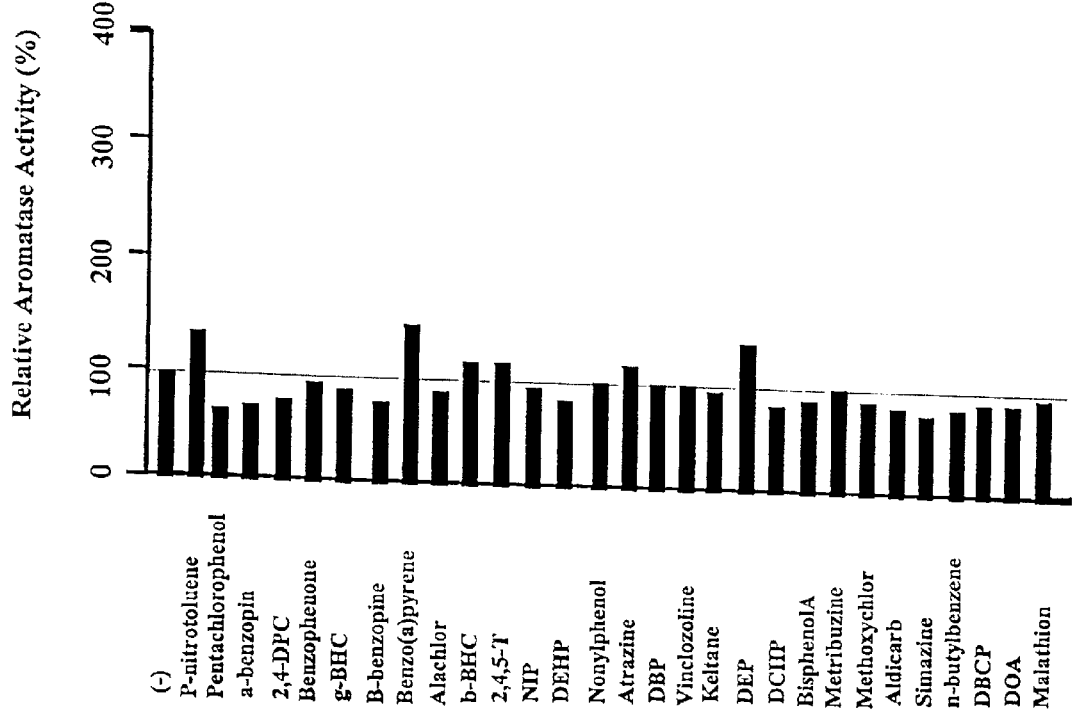

METHOD FOR IDENTIFYING ENDOCRINE DISRUPTORS AND KIT FOR CARRYING OUT THE SAME

FIELD OF THE INVENTION

The present invention relates to a method for identifying an endocrine disruptor using a cell line having aromatase activity, particularly, a human granulosa-like tumor cell line; and a kit for carrying out the method.

BACKGROUND OF THE INVENTION

The use of tributyltin (TBT) as a biocide in antifouling paints and wood preservatives leads to the contamination of the marine and freshwater environment with TBT. TBT has been shown to be highly toxic to a number of aquatic animals. Especially in marine prosobranch snails, TBT induces reproductive abnormalities and sterilization in female animals. This phenomenon, which has been called either pseudohermaphroditism or imposex, is characterized by the development of male sex organs (penis and/or vas deferens and prostate tissue) on females (Bryan et al, *J. Mar. Biol. Ass. UK*, 66:611–640 (1986); and Gibbs et al, *J. Mar. Biol. Ass. UK*, 66:767–777 (1986)). Not only TBT, but also triphenyltin (TPT) has been shown to have a strong effect on the development of imposex in the rock shell, *Thais clavigera* (Horiguchi et al, *Environ. Pollution*, 95:85–91 (1997)). However, the detailed biochemical mechanism of this phenomenon remains obscure. The involvement of sex steroids in the expression of imposex in marine neogastropods has been suggested based on the fact that pure female displays the lowest testosterone content, whereas advanced imposex stages have the highest testosterone content (Bettin et al, *Helgolander Meeresunters*, 50:299–317 (1996)), as well as the fact that the TBT-induced imposex is completely suppressed by antiandrogen cyproterone acetate, which is a competitive inhibitor of androgen receptors (Bettin et al, supra). TBT-induced imposex is mediated by an increasing androgen levels relative to estrogen levels, thus suggesting a decreased conversion of androgens to estrogens, i.e., aromatization (Bettin et al, supra; and Spooner et al, *Mar. Environ. Res.*, 32:37–49 (1991)). This has been further supported by the fact that a specific aromatase inhibitor, SH489, exhibited the same imposex-inducing effect in neogatropods as did TBT-exposure (Bettin et al, supra). On the other hand, there is a controversial report which demonstrated no decrease in the activity of aromatase in gastropods, which were contaminated and exhibited clear evidence of imposex (Morcillo et al, *Environ. Res.*, 81:349–354 (1999)). There is yet no clear direct in vitro evidence demonstrating that TBT compounds truly affect aromatase activity in any species, including marine species, as well as in humans.

A low dose of Dioxin or PCB, is known to cause problems in sperm formation in males that affects rates of hypospadias and cryptorchism. An orchioncus rise results which is passed to the next generation. Further, it is known that the pesticide Benomyl, can cause man sterility.

Thus, long-term and excessive exposure to endocrine disruptors in humans causes clinical problems, which relate to excessive androgens and/or reduced estrogens. Clinical problems in women include ovarian dysfunction, osteoporosis and hirsutism. Clinical problems in men include sterility. Hence, it is important to be able to identify endocrine disruptors so that exposure to the same can be eliminated.

A steroidogenic human ovarian granulosa-like tumor cell line, KGN, from a patient with invasive granulosa cell carcinoma has been established (Nishi et al, *Endocrinol.*, 142:437–445 (2001); which is incorporated by reference herein in its entirety). The cell line possesses properties very similar to normal ovarian granulosa cells, including the expression of functional FSH receptor and a relatively high aromatase activity.

The KGN cell line was found in the present invention to be a useful model for investigating the in vitro effects of various compounds on aromatase activity in the mammalian system, and thus useful in identifying compounds which are effective as endocrine disruptors.

SUMMARY OF THE INVENTION

An object of the present invention is to provide a cell line useful for investigating the effects of compounds on aromatic activity.

Another object of the present invention is to provide a method for identifying an endocrine disruptor.

Still another object of the present invention is to provide a kit for carrying out said method.

These and other objects of the present invention, which will be apparent from the detailed description of the present invention provided hereinafter, have been met in one embodiment by a method for identifying an endocrine disruptor comprising the steps of:

(a) incubating a cell line having aromatase activity with a test compound;

(b) assaying for inhibition or activation of aromatase activity due to said test compound so as to identify an endocrine disruptor.

BRIEF DESCRIPTION OF THE DRAWINGS

FIGS. 5A–5B show the effect of various compounds on relative aromatase activity (% of control) in cultured KGN cells using the same method set forth in Example 3. In FIGS. 5A–5B, P-nitrotoluene is the same as 4-Nitrotoluene; 2,4-DPC is a 2,4-Dichlorophenol; a-benzopin means α-benzopin; b-BHC means β-BHC; and g-BHC means γ-BHC.

DETAILED DESCRIPTION OF THE INVENTION

Figure 1:
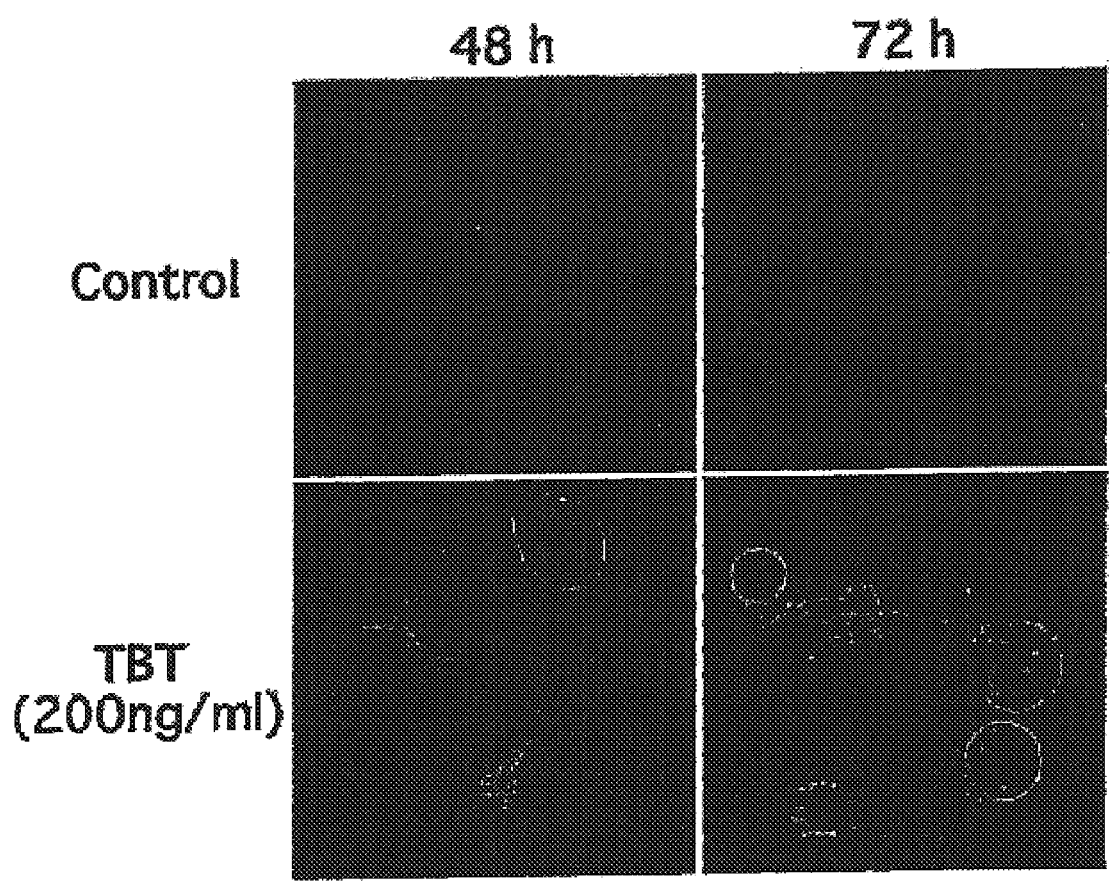
FIG. 1 shows the morphological effects of TBT on KGN cells, using an Annexin V-EGFP/PI Apoptosis Kit and fluorescence microscopy.

As discussed above, in one embodiment the above-described objects of the present invention have been met by a method for identifying an endocrine disruptor comprising the steps of:

(a) incubating a cell line having aromatase activity with a test compound;

(b) assaying for inhibition or activation of aromatase activity due to said test compound so as to identify an endocrine disruptor.

As used herein the expression "endocrine disrupter" is a compound which disrupts normal regulation of the endocrine system, i.e., a compound which inhibits or activates aromatase activity.

Examples of known endocrine disruptors include: Dioxin, Polychlorinated biphenyls (PCBs), Polybrominated biphenyls (PBBs), Hexachlorobenzene (HcB), Pentachlorophenol (PCP), 2,4,5-Trichlorophenoxy acetic acid (2,4,5-T), 2,4-Dichlorophenoxyacetic acid (2,4-D), Amitrole (3-Amino-1,2,4-triazole), Atrazine, Alachlor, Simazine (CAT), Hexachlorocyclohexane (HCH, BHC), Ethyl parathion (Parathion), Carbaryl (NAC), Chlordane (oxychlordane and trans-Nonachlor), 1,2-Dibrome-3-chloropropane (DBCP), DDT (DDE and DDD), Kelthane (Dicofol), Aldrin, Endrin, Dieldrin, Methomyl, Endosulfan (Benzoepin), Heptachlor and Heptachlor epoxide, Marathion, Methoxychlor, Mirex, Nitrofen (NIP), Toxaphene, Organotin compounds such as TBT or TPT, Trfuralin, Alkyl phenol such as Nonylphenol or Octylphenol, Bisphenol A, Di-2-ethylhexyl phthalate (DEHP), Butylbenzyl phthalate (BBP), Di-n-butyl phthalate (DBP) Dicyclohexyl phthalate (DCHP), Diethyl phthalate (DEP), Benzo (a) pyrene, 2,4-Dichlorophenol (2,4-DPC), Di(2-ethylhexyl)adipate, Benzophenone, P-Nitrotoluene, 4-Nitrotoluene, Octachlorostyrene, Aldicarb, Benomyl, Kepone, Mancozeb, Maneb, Metiram, Metribuzine, Cypermethrin, Esfenvalerate, Fenvalerate, Permethrin, Vinclozoline, Zineb, Ziram, Di-n-pentyl phthalate (DPP), Dihexyl phthalate (DHP), Dipropyl phthalate (DprP), Styrene dimers and trimers, N-Butyl benzene, Estradiol, Diethlhexyl adipate, Diethlhexyl adipate (DOA), trans-cholordane, cis-cholordane, p-(1,1,3,3-Tetramethlbutyl) phenol (TMBP), (2,4-Dichlorophenoxy)acetic acid (2,4-PA), Cd, Pb, and Hg.

The particular cell line cell line having aromatase activity employed in the present invention is preferably a human cell line, more preferably, a human granulosa-like tumor cell line. In an even further preferred embodiment, the cell line is KGN cell line (RIKEN gene bank deposit number: RCB 1154). The KGN cell line has the following characteristics:

(a) Origin: female invasive ovarian granulosa cell carcinoma;

(b) Doubling time: 46.4 h;

(c) Abnormal karyotype: 45, XX, 7q-, -22 (7q deletion and monosomy 22);

(d) possesses aromatase activity;

(e) produces progesterone upon exposure to human chorionic gonadotropin (HCG); and (f) expresses follicle stimulating hormone (FSH).

Assaying for inhibition or activation of aromatase activity may be carried out by measuring the amount of [$^3$H]H$_2$O released upon conversion of [1β-$^3$H]androstenedione to estrone using a modification of the method of Ackerman et al, *J. Clin. Endocrinol. Metab.*, 53:412–417 (1981), or as described in Example 3 below. Briefly, the cells are plated on a petri dish (Falcon 3001) in culture medium with 10% (v/v) fetal calf serum (FCS). At confluence, the culture medium is replaced with DMEM/Ham's F-12 containing 5.0–10% (v/v) dextran-coated, charcoal-treated FCS (DCS) (Hyclone, Logan Utah.), and incubated for another 12 h in the presence or absence of $10^{-5-10^{-2}}$ M db-cAMP (Wako Pure Chemical Industries Ltd.) and the test compound. After treatment, the cells are further incubated with 12.5 nM [1β-$^3$H] androstenedione (NEN Life Science Products, Boston, Mass.; SA, 27.5 Ci/mmol) for 6–12 h. After incubation, the medium (2.0 ml) is transferred to tubes containing 1.0 ml ice-cold 30% (w/v) trichloroacetic acid (TCA), and then centrifuged to remove precipitated protein. The cells are harvested using 0.25% (w/v) trypsin-1.0 mM EDTA to determine the protein concentration. The protocol for the extraction of the medium to measure the amount of [$^3$H]H$_2$O is performed as described by Tanaka et al, *Calcif. Tissue Int.*, 52:107-109 (1993). Finally, the amount of radioactivity in the [$^3$H]H$_2$O is corrected by subtracting the blank values from each sample. The cell protein content is determined using a micro bicinichoninic acid kit (Pierce Chemical Co., Rockford, Ill.) after the cells are dissolved in 1.0 N NaOH. The aromatase activity is expressed as picomoles per mg cell protein. As a control, the aromatase activities of human granulosa cells (obtained from in vitro fertilization programs), human fibroblast, and HOS cell (human osteoblast-like cell line) (Tanaka et al, supra) can be measured in the same manner.

KGN cells do not normally produce estrone and estradiol. However, if androstenedione, which is the substrate of aromatase, is added, the KGN cells produce estrone and estradiol from androstenedione. Thus, aromatase activity can also be measured by measuring the amount of estrone or estradiol produced by KGN cells. Briefly, KGN cells are cultured, then the culture medium is replaced with DMEM/Ham's F-12 containing 5.0% (v/v) DCS (Hyclone, Logan Utah.) for 24 h. Next, various concentrations of the test sample (usually $10^{-12-10^{-6}}$ M) are added to the cells, and incubated 48 hr. After incubation, $10^{-6}$ M 4-androstene-3-17-dione is added to the cells, which are further incubated for 72 hr. The culture medium is collected and the amount of estrone or estradiol secreted into the culture medium is measured using a commercially available ELISA or RIA (SRL, Inc., Tokyo, Japan). Aromatase activity is calculated as a relative activity against a solvent control (without test sample) as 100%. The concentration of the test sample may be plotted on an X axis, and the percentage of the amount of estrone as aromatase activity on a Y axis.

In another embodiment, the above-described objects of the present invention have been met by a kit for screening for an endocrine disruptor comprising the cell line having aromatase activity, and components for assaying for inhibition of aromatase activity. Examples of such components and amounts thereof include 0.1–50 nM [1β-$^3$H] androstenedione, $10^{-4}-10^{-2}$ M db-cAMP, 50–500 ng/ml of follicle stimulating hormone (FSH), $10^{-8-10^{-5}}$ M dexamethasone or 50–5000 mIU/ml of menopausal gonadotropin (MG), and preferred medium for cultivating the cells which have aromatase activity, such as a 1:1 mixture of DMEM/Ham's F-12 containing 5.0% (v/v) DCS. FSH, dexamethasone and MG have activities similar to db-cAMP in terms of stimulating aromatase activity.

The following examples are provided for illustrative purposes only, and are in no way intended to limit the scope of the present invention.

EXAMPLE 1

Isolation of KGN Cell Line

A 63-yr-old woman with a tumor in her pelvic space was admitted to the gynecology division of Kyushu-Rosai Hospital in April 1984. After a series of clinical and laboratory examinations, a diagnosis of ovarian cancer stage III was made, and a surgical operation (total abdominal hysterectomy, bilateral salpingo-oophorectomy, and omentectomy) was performed in May 1984. The histopathological diagnosis indicated granulosa cell carcinoma. In December 1993, the tumor recurred in the pelvic region. A portion of the granulosa tumor tissue obtained at the time of reoperation in January 1994 was used as the source of the cell culture.

A specimen of enucleated granulosa tumor tissue was finely minced and dispersed into cells by treatment with 0.25% (w/v) collagenase at 37° C. for 1 h. Thereafter, the cells were cultured for several passages in a 1:1 mixture of DMEM and Ham's F-12 medium supplemented with 10% (v/v) FCS (Sera Laboratory Ltd., Sussex, UK), 100 U/ml of penicillin, 100 μg/ml streptomycin, and HITES ($10^{-8}$ M hydrocortisone, 5.0 μg/ml of insulin, 100 μg/ml of transferrin, $10^{-8}$ M 17β-estradiol, and $3\times10^{-8}$ M sodium selenite) (Gazdar et al, *Cancer Res.*, 50:5488–5496 (1990)). After the 10th passage, the amounts of HITES in the culture medium were gradually decreased. After the 15th passage, the cells were maintained in a DMEM/Ham's F-12 medium supplemented with 10% (v/v) FCS alone. After that, the cells were passaged every 1–2 weeks with 0.25% (w/v) trypsin-1.0 mM EDTA, and a morphologically homologous cell population, designated KGN was thus obtained. KGN was determined to have the following properties:

(a) a doubling time of 46.4 h;

(b) an abnormal karyotype: 45, XX, 7q-, -22 (7q deletion and monosomy 22);

(c) possesses aromatase activity;

(d) produces progesterone upon exposure to human chorionic gonadotropin (HCG); and (e) expresses follicle stimulating hormone (FSH).

The KGN cell line has been deposited at the RIKEN gene bank, deposit number: RCB 1154 and deposited at the International Patent Organism Depository of the NIAIST in Japan on Aug. 29, 2002 under deposit number FERM-8171.

The cells were maintained in DMEM/F-12 supplemented with 10% (v/v) FCS in an atmosphere of 5% $CO_2$ at 37° C. DMEM/F-12 and FCS were purchased from Gibco BRL (Grand Island, N.Y., USA).

EXAMPLE 2

The Effects of TBT and TPT on KGN Cell Growth

The KGN cells possess properties similar to those of normal granulosa cells, including the expression of functional FSH receptor and a relatively high aromatase activity, as well as 17β-hydroxysteroid dehydrogenase (17β-HSD) activity. The KGN cell line can thus, produce estrogens, such as estrone (E1) and estradiol (E2), in the presence of exogenous substrate, 4-androstene-3,17-dione.

Since TBT and TPT are well-known to be toxic to several cells or to cause apoptosis (Stridh et al, *Toxicol. Appl. Pharmacol.*, 156:141–146 (1999)), the effect of TBT and TPT on growth of KGN cells was evaluated. TBT and TPT were obtained from the Sigma Chemical Co. (St. Louis, Mo.). Further, both compounds were dissolved in ethanol, and the final concentration of ethanol in the cell growth medium was 0.1% (w/v).

More specifically, the cells were plated onto a 24-well plate at $1\times10^4$ cells/well in DMEM/F-12 supplemented with 10% (v/v) FCS. The cells were then treated with various concentrations of TBT or TPT, while control cells were treated with ethanol alone. The medium treated with the TBT or TPT, or ethanol was changed every 2 days. After washing, the cells were trypsinized and then counted using a hemocytometer every 48 h for 7 days. Cell viability was assessed by the trypan blue exclusion method.

More than 1000 ng/ml of TBT or TPT were found to be very toxic to KGN cells, and all of the cells died within 24 h.

Next, apoptosis in the KGN cells treated with TBT was detected by fluorescence microscopy. More specifically, early and late apoptotic changes in the cells were determined using an Annexin V-EGFP/PI Apoptosis Detection Kit, as described by Mu et al, *Endocrinol.*, 142:3590–3597 (2001). One day before treatment, the cells were divided into 35-mm glass-bottom dishes (MatTek Corporation), and then treated with 200 ng/ml TBT for 48 h and 72 h, respectively. After the treatment, the cells were washed once with phosphate-buffered saline (PBS), and then incubated with 200 ml of 1×binding buffer comprising 1.0 ml annexin V-EGFP and 1.0 ml propidium iodide (PI) at room temperature for 5 min in the dark. The cells were then scanned using a confocal laser scanning microscopy (Leica TCS-SP system, Leica Microsystems, Heidelberg, Germany) using a dual filter set for FITC & TRITC. The cell membrane was imaged for green fluorescence (stained by annexin V-EGFP) by excitation with the 488 nm line from an argon laser, and the emission was viewed through a 460 to 505 nm band pass filter. The cell nucleus was imaged for red fluorescence (stained by PI) by excitation with the 560 nm line from an argon laser, and the emission was viewed through a 520 to 580 nm band pass filter. The results are shown in FIG. 1.

As shown in FIG. 1, at a concentration of 200 ng/ml of TBT for 48 h, cell proliferation was suppressed to almost 50% of untreated cells, and some apoptotic cells were observed by Annexin V-EGFP/PI staining. Annexin V binds with a high affinity to negative charged PS, and it has been used in combination with PI to detect early and late apoptotic or necrosis cells. In unexposed control cells, most cells stained for neither annexin V-EGFP (green) nor PI (red). After being treated with 200 ng/ml TBT, early apoptotic cells with a cell membrane stained by green color (annexin V positive/PI negative) were detected at 48 h, and late apoptotic cells with a cell membrane demonstrating green staining and red staining for nuclear staining (annexin V positive/PI positive) were seen at 72 h. However, TBT and TPT at concentrations of less than 50 ng/ml (2 or 20 ng/ml) had little effect on KGN cell proliferation for 7 days. As a result, a concentration of 20 ng/ml of TBT or TPT, which has been reported to induce imposex in marine species, was used in the following experiment.

EXAMPLE 3

The Effects of TBT and TPT on Aromatase Activity

To evaluate the effect of TBT and TPT on aromatase activity in KGN cells, the cells were incubated with 20 ng/ml TBT or TPT for 72 h in the presence or absence of $10^{-4}$ M db-cAMP, and then aromatase activity was assessed by a [$^3$H]H$_2$O release assay. db-cAMP was purchased from the Sigma Chemical Co. (St. Louis, Mo.).

More specifically, aromatase activity was determined by measuring [$^3$H]H$_2$O release upon conversion of [1β-$^3$H] androstenedione (A) to estrone (E1), as described by Mu et al, *Biochem. Biophys. Res. Commun.*, 271(3):710–713 (2000). [1β-$^3$H]androstenedione was purchased from Amersham Pharmacia Biotech (Boston, Mass.).

Initially, the cells were cultured in DMEM/F-12 with 5.0% (v/v) DCS for 48 h. After the cells were treated with either TBT or TPT as described above, [1β-$^3$H] androstenedione was added, and the cells were further incubated for 6 h. The medium (2.0 ml) was extracted with chloroform, and was then centrifuged. The aqueous supernatant was mixed with 5.0% (w/v) charcoal/0.5% (w/v) dextran, and incubated for 30 min. Thereafter, the mixture was centrifuged and the supernatant was added to 5.0 ml of scintillation fluid and assayed for radioactivity. The amount of radioactivity in [$^3$H]H$_2$O thus measured was standardized based on the protein concentration, which was determined using a micro BCA kit (Pierece Chemical Co., Rockford, Ill.), and expressed as pmol/mg protein/6 h. The results are shown in FIG. 2A.

Figure 2A:
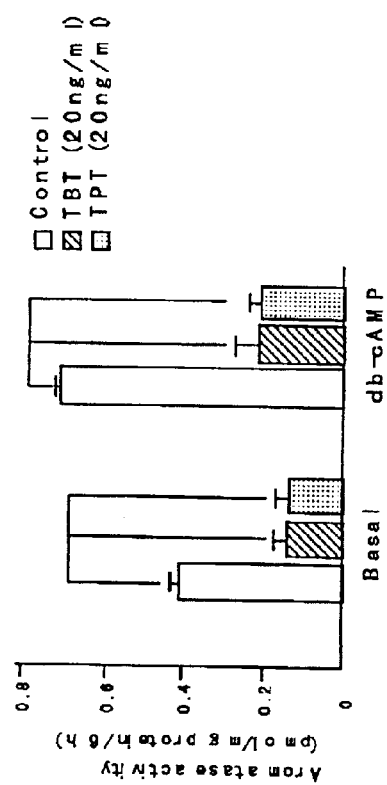
FIG. 2A shows the effect of TBT and TPT on aromatase activity in cultured KGN cells in the presence or absence of $10^{-4}$ M dibutyryl cyclic AMP (db-cAMP). The data represent the mean±SD from three independent experiments done in triplicate. *, P<0.01 vs. control cells treated with ethanol.

As shown in FIG. 2A, the basal level of aromatase activity in KGN cells was 0.435±0.041 pmol/mg protein/6 h. TBT or TPT slightly, but significantly, inhibited aromatase activity to about 30% of the baseline (P<0.05). While $10^{-4}$ M db-cAMP treatment gave rise to a 1.7-fold increase in aromatase activity over baseline, the increase was also suppressed by 20 ng/ml TBT or TPT.

Figure 2B:
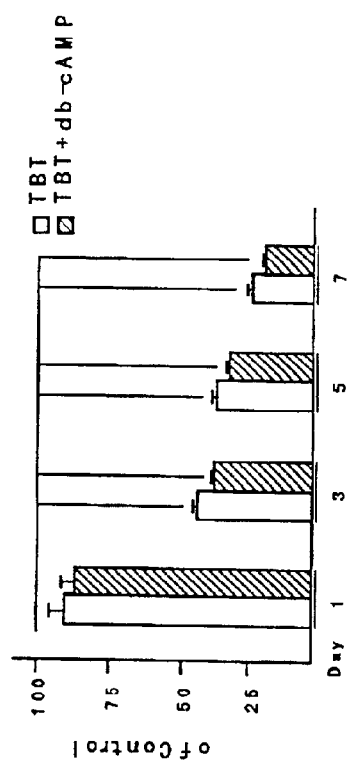
FIG. 2B shows the effect of 20 ng/ml TBT on aromatase activity in the presence or absence of $10^{-4}$ M db-cAMP over a 7-day period. The data represent the mean±SD from three independent experiments done in triplicate. *, P<0.01 vs. control cells treated with ethanol.

Next, the effect of 20 ng/ml TBT on basal or $10^{-4}$ M db-cAMP-stimulated aromatase activity was investigated over a 7-day period. The results are shown in FIG. 2B. In FIG. 2B, the aromatase activity of control cells is expressed as 100 and the relative aromatase activity treated with 20 ng/ml TBT+$10^{-4}$ M db-cAMP is expressed as "of control".

As shown in FIG. 2B, a significant inhibition of aromatase activity was observed either in a basal state or in states stimulated by $10^{-4}$ M db-cAMP, respectively, as early as 3 days after the addition of TBT, and a maximal inhibition was observed at day 7.

The aromatase activity determined by the [$^3$H]H$_2$O release assay did not definitively verify the capability of estrogen production in KGN cells. Thus, the db-cAMP stimulated E2 production in KGN cells with or without TBT or TPT treatment for 7 days was assessed. To ensure that the measured aromatase activity truly reflected the capability of estrogen production, the cells were treated with or without various concentrations (2 or 20 ng/ml) of TBT or TPT for 7 days, and then were further incubated with 1.0 mM 4-androstene-3,17-dione for 12 h. The media was collected and the E2 content in the media was determined by specific RIA (SRL, Inc. Tokyo, Japan). The results are shown in FIG. 2C.

Figure 2C:
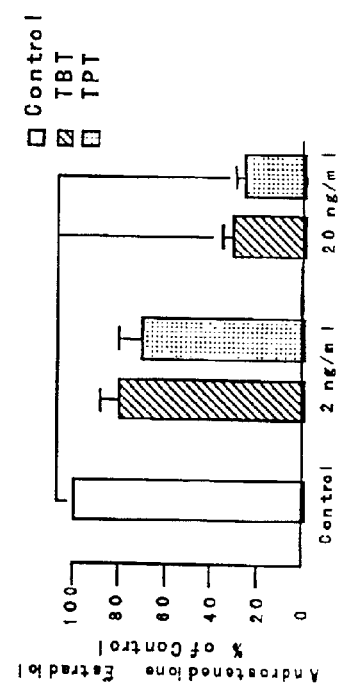
FIG. 2C shows the effect of TBT and TPT on estradiol (E2) production in cultured KGN cells. The data represent the mean±SD from three independent experiments done in triplicate. *, P<0.05 vs. control cells treated with ethanol.

As shown in FIG. 2C, treatment with 20 ng/ml TBT or TPT for 7 days caused a significant decrease in E2 concentration in the medium, which was consistent with the changes observed in aromatase activity.

EXAMPLE 4

The Effect of TBT on P450arom mRNA

In females, estrogens are mainly synthesized in ovarian granulosa cells before menopause, and are produced by the conversion of androgens. The biosynthesis of estrogens from androgens is catalyzed by an enzyme complex which has been called aromatase (CYP 19, cytochrome P450arom) (Simpson et al, *Endocr. Rev.*, 15:342–355 (1994)). P450arom is present in many tissues, including the gonads, brain, placenta, bone and adipose tissue (Simpson et al, supra; Longcope et al, *J. Clin. Endocrinol. Metab.*, 46:146–152 (1978); Sasano et al, *Endocr. Rev.*, 19:593–607 (1998); and Townsley et al, *Am. J. Obstet. Gynecol.*, 117:345–350 (1973)).

To investigate whether or not the observed changes in aromatase activity in KGN cells were associated with comparable changes in the levels of cytochrome P450 aromatase (P450arom) mRNA, total RNA was extracted from cells maintained in the absence or presence of 20 ng/ml of TBT for 48 h. RNA extraction and RT-PCR analysis for P450arom mRNA were performed as described by Ikuyama et al, *Clin. Endrocrinol.*, 48(5):647–654 (1998). Taq DNA polymerase was obtained from Promega (Madison, Wis.). All of the primers for the PCR were synthesized by Amersham Pharmacia Biotech (Osaka, Japan). The PCR products were electrophoresed on 2.0% (w/v) agarose gel containing 0.5 mg/ml ethidium bromide. The results are shown in FIG. 3B.

The relative expression levels of P450arom vis-à-vis β-actin were determined by the measuring of the intensity of the ethidium bromide. The results are shown in FIG. 3A.

Figure 3A:
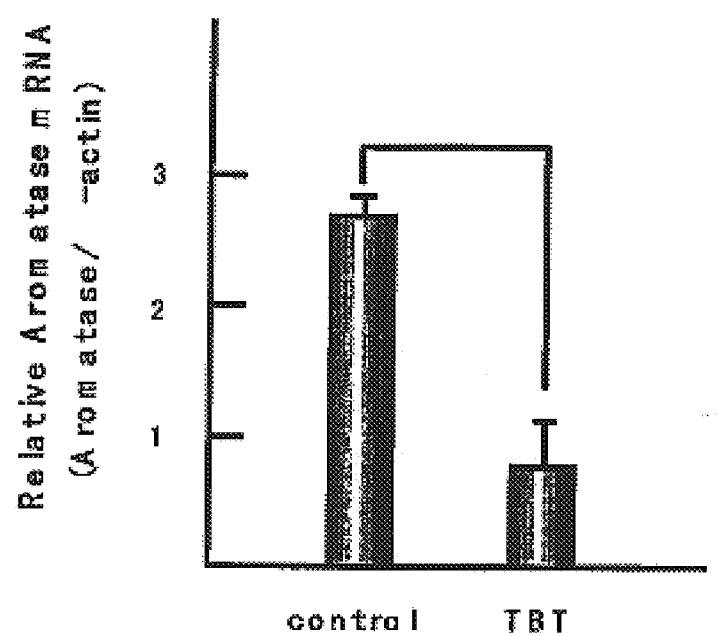
FIG. 3A shows the effect of TBT on P450arom mRNA expression relative to that of β-actin in cultured KGN cells. The data represent the mean±SD from three experiments done in triplicate. *, P<0.05 vs. control cells treated with ethanol.
Figure 3B:
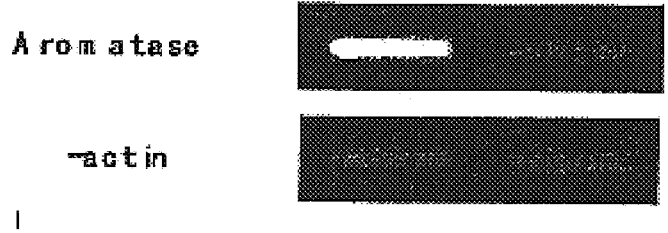
FIG. 3B shows the relative expression levels of P450arom mRNA and β-actin in KGN cells.

As shown in FIG. 3A, changes in the P450arom mRNA levels were associated with comparable changes in aromatase activity. Therefore, the decrease in aromatase activity of KGN cells treated with TBT was related to the decrease in P450arom mRNA levels.

EXAMPLE 5

Luciferase Activity

The tissue-specific expression of the P450arom gene is mediated by tissue-specific promoters using alternative splicing of exon 1 (Harada et al, *Proc. Natl. Acad. Sci. USA*, 90:11312–11316 (1993); and Mahendroo et al, *J. Biol. Chem.*, 268:19463–19470 (1993)). In ovarian granulosa cells, promoter II in the CYP 19 gene is mainly utilized for its transcriptional regulation. In addition, the transcriptional regulation of the P450arom gene in ovarian granulosa cells has been demonstrated to be activated by the cAMP-protein kinase A pathway and is also dependent on a steroidogenic tissue-specific transcriptional factor, Ad4BP/SF-1 (Carlone et al, supra; and Richards et al, *Encocrinol.*, 114:2190–2198 (1984). Further, it has been reported that cooperative or additive interaction between Ad4BP and CREB (cAMP-regulatory element binding protein) is required for cAMP activation of promoter II in granulose cells (Carlone et al, supra)

Figures 4A, 4B:
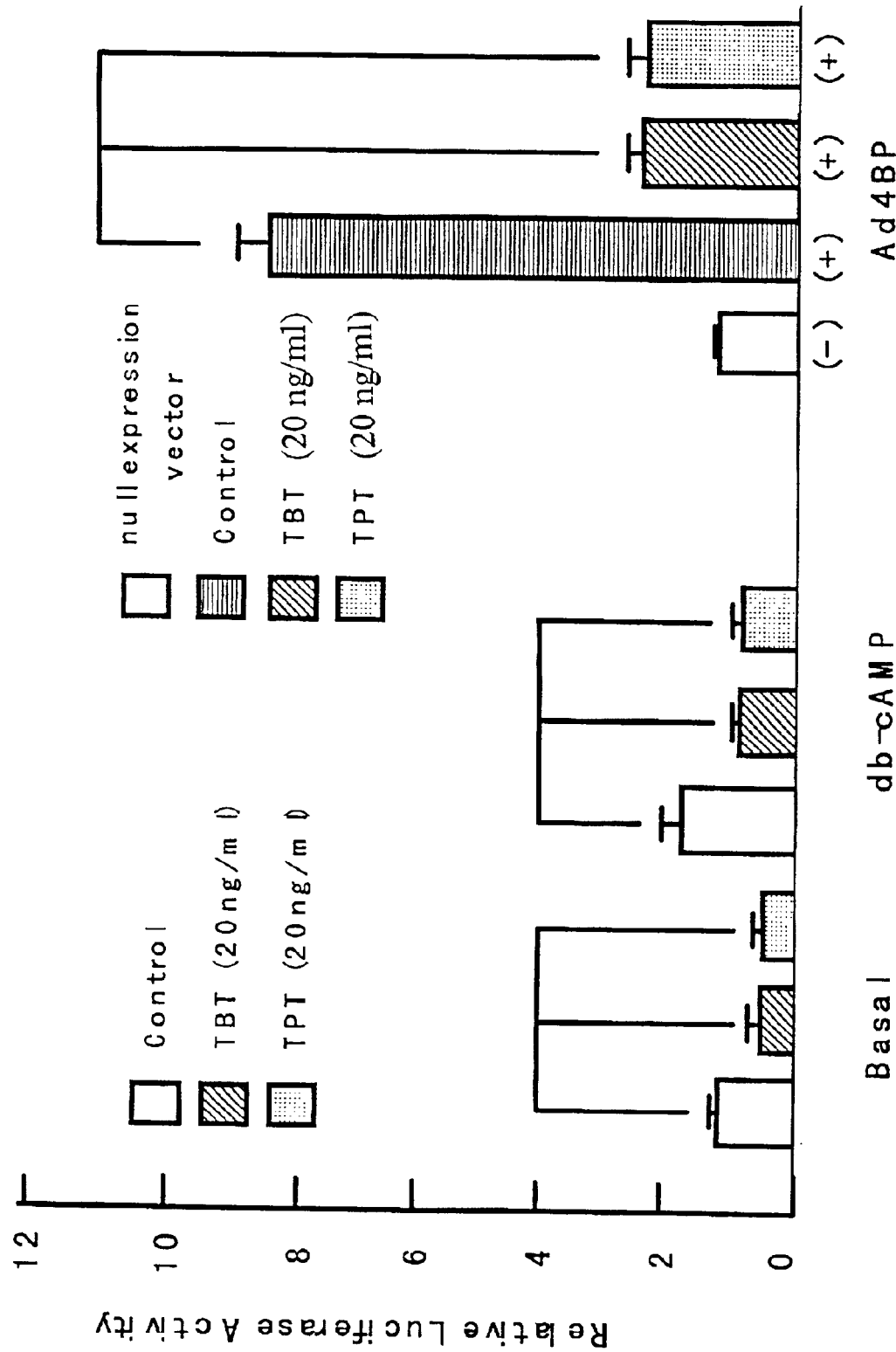
FIG. 4A shows the effect of TBT and TPT on luciferase activity controlled by the P450arom promoter II in KGN cells. The data represent the mean±SD from three experiments done in triplicate. *, P<0.01 vs. control cells treated with ethanol.
FIG. 4B shows the effect of TBT and TPT on luciferase activity controlled by the P450arom promoter II when co-transfected into KGN cells with bovine Ad4BP expression vector (RSV/Ad4BP) or a null expression vector as a negative control. The data represent the mean±SD from three experiments done in triplicate. *, P<0.01 vs. control cells treated with ethanol.

Thus, to determine whether or not the decreased expression of P450arom mRNA was regulated through promoter II, which is the major promoter in ovarian granulosa cells (Nishi et al, *Endocrinol.*, 142:437–445 (2001); Means et al, *Mol. Endocrinol.*, 5:2005–2013 (1991); and Carlone et al, *Mol. Endocrinol.*, 11:292–304 (1997)), luciferase activity was determined using a 1 kb P450arom promoter II expression construct in the luciferase reporter vector, pGL3 (Mu et al, *Mol. Cell. Endocrinol.*, 181:239–248 (2001)). pGL3 was obtained from Promega (Madison, Wis.). Transfection was performed using SuperFect reagents according to the manufacturer's instructions (Qiagen (Hilden, Germany)). More specifically, 1×10$^5$ cells were seeded in a 6-well plate 12 h prior to transfection, and transfected with 2.0 µg of DNA. Five nanograms of Renilla luciferase control reporter vector, pRL-CMV, obtained from Promega (Madison, Wis.), as an internal standard, were added per well to assess the transfection efficiency. On the day after transfection, the cells were treated with or without 20 ng/ml TPT or TBT in the presence or absence of $10^{-4}$ M db-cAMP. The cells were maintained at 37° C. for 48 h, and then lysed and harvested, and thereafter subjected to a luciferase analysis using the Dual-luciferase reporter assay system according to the manufacturer's instructions (Promega (Madison, Wis.)). The results are shown in FIGS. 4A–4B. The promoter activity determined is shown as a fold-increase in the luciferase activity normalized for Renilla luciferase activity (termed relative luciferase activity).

As shown in FIG. 4A, the luciferase reporter driven by P450arom promoter II displayed a 100-fold higher luciferase activity compared with $10^{-4}$ M db-cAMP, which induced a 1.7-fold activation of the promoter. The luciferase activity was decreased by the addition of TBT or TPT in transfected cells either in a basic state or in states stimulated by db-cAMP, respectively.

In addition, as shown in FIG. 4B, the forced expression of Ad4BP/SF-1 caused an 8-fold activation of the promoter. The Ad4BP/SF-1-dependent increase of the luciferase activity was also significantly suppressed by both TBT and TPT.

EXAMPLE 6

The Effects of Additional Compounds on Aromatase Activity

The method described in Example 3 was repeated but instead of using TBP or TPT, the compounds shown in FIGS. 5A–5B were tested, including Benomyl, Heptachlor, and Benzopyrene. The results are shown in FIGS. 5A–5B.

As shown in FIGS. 5A–5B, compounds such as Benomyl, Heptachlor, and Benzopyrene, which are known endocrine disruptors, were surprisingly found to activate aromatase activity in KGN cells. As discussed above, Benomyl, a pesticide, can cause sterility in men. It is believed in the present invention that such sterility is due, at least in part, to activation of aromatase activity, giving rise to excessive estrogen exposure.

As shown herein, inter alia, treatment with TBT or TPT directly inhibits aromatase activity in a cultured human granulosa-like tumor cell line, KGN cells, either at a basic state or in states stimulated by db-cAMP. This finding is further supported by the actual decrease of E2 concentration in the cultured medium. The inhibitory effect of aromatase activity by TBT and TPT in KGN cells is clearly not due to competitive inhibition of P450arom, because the inhibitory effect of TBT and TPT occurs very slowly (more than 48 h), which was a striking contrast to a rapid (within 5 min) and complete suppression of the aromatase activity when using a competitive aromatase inhibitor, YM511 in the same culture system. YM511 was kindly provided by Yamanouchi Pharmaceuticals (Tokyo, Japan) (Kudoh et al, *J. Steroid Biochem. Mol. Biol.*, 54:265–271 (1995)). The changes in aromatase activity caused by TBT was associated with comparable changes in the P450arom mRNA level, as assessed by RT-PCR. In addition, the luciferase activity of P450arom promoter II (1 kb) decreased after the addition of TBT and TPT in transfected KGN cells either at a basal state or in states stimulated by db-cAMP. Ad4BP/SF-1-dependent increase of the luciferase activity of P450arom promoter II was also down-regulated by such treatments. Based on the above findings, TBT-induced suppression of aromatase activity is believed to be partly regulated at the transcriptional level in association with the cAMP-PKA pathway or regulation by Ad4BP/SF-1. However, at least the expression level of Ad4BP determined by RT-PCR was unchanged by treatment with TBT or TPT.

The dose ranges of TBT and TPT that inhibited aromatase activity were 2–20 ng/ml (corresponding to 0.6–6 nM), which are pharmacologically relevant to the ranges which are reported to induce imposex in female gastropods (Bryan et al, supra; Gibbs et al, supra; and Horiguchi et al, supra). While the species are different, the findings herein support the previously reported hypothesis that TBT disturbs aromatase activity, thus leading to the induction of imposex in female aquatic animals (Bryan et al, supra; Gibbs et al, supra; Horiguchi et al, supra; Bettin et al, supra; and Spooner et al, supra). Thus, long-term and excessive exposure to TBT in humans is believed to also cause clinical problems which relate to excessive androgens and/or reduced estrogens, especially in women, such as ovarian dysfunction, osteoporosis and hirsutism. Induction of apoptosis of granulosa cells at higher concentrations of TBT is believed to indicate that a more TBT-polluted environmental situation can cause much more severe ovarian dysfunction.

Another explanation for imposex by organotin compounds in gastropods has been suggested to be the inhibition of androgen excretion due to a decrease in the sulfur conjugation of androgen, although this mechanism remains unclear (Roins et al, *Mar. Environ. Res.*, 42:161–166 (1996)). In addition, as a third explanation, it was recently reported that TBT and TPT are potential activators of androgen-receptor-mediated transcription in mammalian cells (Yamabe et al, *Toxicol. and Appl. Pharmacol.*, 169:177–184 (2000)). Therefore, the mechanism of imposex by organotin is believed to be attributed not simply to aromatase inhibition, but also related to several other factors, including a decrease in sulfur conjugation of androgen and up-regulation of AR-mediated transcription. This is believed to be true because each reported mechanism itself is not sufficient to explain such a dramatic sex reversal like imposex.

While the invention has been described in detail and with reference to specific embodiments thereof, it will be apparent to one skilled in the art that various changes and modifications can be made therein without departing from the spirit and scope thereof.

What is claimed:

1. A method for identifying an endocrine disrupter comprising the steps of:
   (a) incubating a granulosa-like tumor cell line having aromatase activity with a test compound;
   (b) assaying for inhibition or activation of aromatase activity due to said test compound so as to identify an endocrine disrupter.

2. The method of claim 1, wherein said cell line is a human cell line.

3. The method of claim 2, wherein said cell line is a human granulosa-like tumor cell line that has the following characteristics:
   (a) Origin: female invasive ovarian granulosa cell carcinoma;
   (b) Doubling time: 46.4 h;
   (c) Abnormal karyotype: 45, XX, 7q-,-22(7q deletion and monosomy 22);
   (d) Possesses aromatase activity;
   (e) Produces progesterone upon exposure to human chorionic gonadotropin (HCG); and
   (f) Expresses follicle stimulating hormone (FSH).

4. The method of claim 3, wherein said human cell line is KGN cell line (RIKEN gene bank deposit number: RCB 1154).

5. The method of claim 1, wherein aromatase activity is assayed using an assay selected from the group consisting of a [$^3$H]$H_2O$ release assay, an ELISA and an RIA.

* * * * *